(12) United States Patent
Forster

(10) Patent No.: US 6,425,942 B1
(45) Date of Patent: Jul. 30, 2002

(54) METHOD AND DEVICE FOR DRYING A GAS

(75) Inventor: Randolf Ruediger Forster, Boohum (DE)

(73) Assignee: Ruhrgas Aktiengesellschaft (DE)

( * ) Notice: Subject to any disclaimer, the term of this patent is extended or adjusted under 35 U.S.C. 154(b) by 0 days.

(21) Appl. No.: 09/446,482
(22) PCT Filed: Jun. 12, 1998
(86) PCT No.: PCT/EP98/03550
§ 371 (c)(1),
(2), (4) Date: Jun. 13, 2000
(87) PCT Pub. No.: WO98/59021
PCT Pub. Date: Dec. 30, 1998

(30) Foreign Application Priority Data

Jun. 20, 1997 (GB) .......................... 197 26 210
May 16, 1998 (GB) .......................... 198 22 165

(51) Int. Cl.$^7$ .......................................... B01D 53/14
(52) U.S. Cl. ...................... 95/174; 95/179; 95/193; 95/196; 95/209; 95/231; 96/234
(58) Field of Search ................. 96/234, 240, 242; 95/149, 165, 166, 167, 169, 172, 173, 174, 178, 179, 180, 193, 194, 195, 196, 205, 231

(56) References Cited

U.S. PATENT DOCUMENTS

| 2,797,188 A | * | 6/1957 | Taylor, Jr. et al. |
| 3,254,473 A | * | 6/1966 | Fryar et al. |
| 3,255,573 A | * | 6/1966 | Cox, Jr. |
| 3,367,089 A | * | 2/1968 | Scott |
| 3,609,942 A | * | 10/1971 | Alleman |
| 3,824,177 A | * | 7/1974 | Honerkamp et al. |
| 3,867,112 A | * | 2/1975 | Honerkamp et al. |
| 4,026,681 A | * | 5/1977 | Rosekelly |
| 5,006,258 A | * | 4/1991 | Veatch et al. |
| 5,163,981 A | * | 11/1992 | Choi |
| 5,209,762 A | * | 5/1993 | Lowell |
| 5,268,155 A | * | 12/1993 | Yan |
| 5,269,886 A | * | 12/1993 | Brigham, Sr. |
| 5,453,114 A | * | 9/1995 | Ebeling |
| 5,520,723 A | * | 5/1996 | Jones, Jr. |
| 5,643,421 A | * | 7/1997 | Smith |
| 5,665,144 A | * | 9/1997 | Hill et al. |
| 5,766,313 A | * | 6/1998 | Heath |
| 5,788,864 A | * | 8/1998 | Coberly et al. |
| 6,004,380 A | * | 12/1999 | Landreau et al. |
| 6,071,484 A | * | 6/2000 | Dingman, Jr. et al. |

\* cited by examiner

Primary Examiner—Duane S. Smith
(74) Attorney, Agent, or Firm—Blakely Sokoloff Taylor & Zafman

(57) ABSTRACT

The gas which is to be dried is fed into an absorber (1) where it is brought into contact with a glycol in countercurrent. The glycol absorbs the moisture from the gas and impurities. The glycol laden with water and impurities is removed from the absorber (1) via a line (5). It is then regenerated in a reboiler (9) where the water is eliminated by heating. The water-free glycol is passed into a storage vessel (10) from which it can then be refed to the absorber (1). The glycol which is withdrawn from the storage vessel (10) is purified by mixing it with at least half the quantity of water. The mixture is brought to a temperature above cloud point where it is maintained for a predetermined length of time so that the impurities flocculate. The flocculated impurities are removed in a filter (18) arid the purified glycol mixed with water is refed to the reboiler (9) via a line (19). The drying process is very economical as it integrates environmentally-friendly and simple purification of the glycol.

17 Claims, 3 Drawing Sheets

METHOD AND DEVICE FOR DRYING A GAS

BACKGROUND OF THE INVENTION

1. Field of the Invention

The present invention relates to a method and an arrangement for drying a gas, in particular natural gas, using a glycol as well measures to purify contaminated glycol in a gas drying plant.

2. Related Art

Glycols, in particular triethylene glycol, are used in great quantities to dry gases, in particular natural gas. When natural gas is transported at high pressure, the water vapour content must not exceed a certain amount which depends on the pressure. Condensed water may cause pipeline corrosion. Gas hydrates might also form.

In order to reduce the water content of the gas, it is brought into contact with glycol as an absorbent in drying plants. For example, the gas to be dried and glycol act on each other in countercurrent in an absorber. During this process, the glycol not only absorbs the moisture from the gas but also impurities and leaves the absorber laden with water and impurities. It is then regenerated, the water from the glycol-water mixture being eliminated.

The U.S. Pat. No. 5 490 873 teaches a method in which the vapours released in the regeneration are partially condensed and then fed into a separator. Three phases are separated from one another in the separator, a gas phase, a liquid hydrocarbon phase and a water phase. The gas phase is compressed and fed to the process. The liquid hydrocarbon phase is withdrawn for use and the water phase is disposed of.

The dried glycol from the regeneration process is then returned to the absorber. During this cycle the glycol becomes more and more contaminated. The impurities include salts, particulate matter, the decomposition products of the glycol as well as organic impurities which have been absorbed from the gas to be dried. Some of the decomposition products of the glycol and the impurities absorbed from the gas to be dried are organic acids, which may lead to a fall in the pH, which in turn may cause increased plant corrosion. Furthermore, these and other organic impurities and decomposition products can lead to foam formation, which reduces the drying properties of the glycol and can lead to high glycol losses.

Therefore, in conventional plants it is necessary to replace or purify the glycol at regular intervals. The glycol removed from the drying plant is normally purified by distillation.

SUMMARY OF THE INVENTION

An object of the present invention is to develop a gas drying process which permits more economic use of the glycol used, in particular extends the life of the glycol.

According to the present invention, this object is achieved by a method for drying a gas using a glycol, wherein the gas is fed into an absorber, brought into contact with glycol in the absorber, the glycol absorbing at least part of the moisture and impurities from the gas, and then the gas is removed from the absorber. The glycol laden with water and impurities is removed from the absorber and regenerated by heating to drive the water out. At least some of the glycol removed from the absorber is purified before or after it is regenerated by mixing it with at least half the quantity of water, bringing the mixture to a temperature above its cloud point, and keeping the mixture at that temperature for a predetermined time, during which time the impurities flocculate, removing the flocculated impurities, and regenerating the glycol by heating it to drive the water out of the mixture. The regenerated glycol may then returned to the absorber. Surprisingly, it was found that a considerable proportion of the impurities in the glycol are absorbed in this way by the floccules forming above the cloud point so that subsequent separation produces sufficiently purified glycol. In particular, impurities such as oil, black sludge and other oxidation products are removed from the glycol during this process. The inventive method is a very cost-effective drying process as it integrates environmentally-friendly and simple purification of glycol.

In one embodiment, the glycol removed from the absorber is purified before its regeneration. The water added during the purification process is driven out together with the water absorbed in the absorber in one regeneration step by heating. In this mainstream process, the entire amount of glycol to be regenerated, i.e. to be freed of water, is always purified before regeneration. As in this process an appropriate amount of water always has to be added to the entire amount of glycol in circulation, a large amount of energy is required to separate the water and the glycol in one regeneration step.

In a further embodiment, part of the glycol previously regenerated is purified. The glycol is first regenerated in the conventional manner by eliminating the water. Some of the regenerated but still contaminated glycol is then passed into a purification process. The rest of the regenerated glycol is fed into the absorber.

After removal of the flocculated impurities, the glycol-water mixture is preferably mixed again and regenerated with the glycol which has been removed from the absorber and is to be regenerated. This side-stream process makes it possible to purify only part of the glycol in the absorber cycle so that the energy required in the regeneration step to drive out the water absorbed from the gas and the water mixed during the purification process can be reduced.

The glycol-water mixture is preferably filtered and/or centrifuged to remove the flocculated impurities. Apart from these fast separation methods, it is also possible to employ alternatives such as sedimentation or flocculation.

In an advantageous embodiment of the method according to the present invention, the glycol-water mixture is passed over a first anion exchanger prior to heating.

The glycol-water mixture is preferably brought to a temperature of approx. 40° C. to 90° C. before purification and kept at that temperature for between 2 and 30 minutes. The temperature, time required and percentage of water in the mixture depend on each other. A higher percentage of water leads to more rapid clouding or flocculation of the impurities; on the other hand a higher percentage of water increases the time and amount of energy required to drive the water out of the mixture. The contaminated glycol is preferably mixed with water, roughly in a ratio of 1:1.

In a further embodiment of the inventive method triethylene glycol (TEG) is used as a desiccant. The contaminated triethylene glycol is mixed with water in a ratio of 1:1 for the purification process and the triethylene glycol-water mixture is brought to a temperature of approx. 75° C. to 85° C. and kept at that temperature for between 5 and 20 minutes. The temperature is above the so-called cloud point. The mixture of water and TEG is preferably passed over an anion exchanger prior to heating.

The object of the present invention is also achieved by a purification method for cleaning glycol contaminated in a gas drying plant. Contaminated glycol laden with water and impurities is removed from the gas drying plant. The glycol removed is mixed with at least half the amount of water. The glycol-water mixture is then passed over a first anion exchanger, anionic surfactants being removed from the mixture. The cloud point is reduced below the temperature of the mixture causing flocculation of the impurities. The flocculated impurities are then removed. The purified glycol-water mixture is returned to a regeneration stage of the gas drying plant where the water is driven out. The glycol removed is preferably removed from the gas drying plant and passed to the purification step at a temperature which is high enough for the temperature of the glycol-water mixture after the removal of the anionic surfactants to be already above the cloud point without it being necessary to additionally heat the glycol-water mixture before or after it has passed through the ion exchanger. to additionally heat the glycol-water mixture before or after it has passed through the ion exchanger.

The inventive method produces excellent purification results; a considerable amount of the impurities in the glycol is absorbed by the floccules which are removed. In particular, the method reliably removes oils, black sludge and oxidation products from the glycol. The inventive method is highly efficient and environmentally-friendly.

The method according to this embodiment of the invention has a number of advantages. The method is more cost-efficient and facilitates continuous operation of a purification plant as the glycol-water mixture either does not have to be heated as much after the addition of the water or does not have to be heated at all. This is achieved by lowering the cloud point, which is based on the following mechanism: The glycol from gas drying plants is very often contaminated by high boiling fats and oils. These substances are present in the glycol in emulsion. Apart from non-ionic fatty alcohol ethoxyylates and sugar surfactants, long-chain anionic carboxylic acids (fatty acids) act as emulsifiers. These substances are dissociated, i.e. charged, in the glycol at the pH of 7 normally set by the addition of amines. Therefore, the micelles of the emulsion containing the impurities also have negative charges which means that they repel each other and counteract a breakdown of the emulsion. Once the anionic surfactants have been removed from the glycol-water mixture in the first ion exchanger, the now uncharged micelles agglomerate and can be more easily eliminated. This leads to a lowering of the cloud point, i.e. the temperature at which the impurities flocculate.

The first ion exchanger is preferably charged with anions of a strong acid, in particular with chloride ions. The ion exchanger resin gives off a metered amount of chloride ions to the glycol-water mixture, the surface-active carboxylic acid anions being absorbed from the mixture (as well as other substances). The ion exchanger can be regenerated by back-flushing with a sodium chloride solution. The release of chloride ions to the glycol-water mixture additionally increases the ion strength of the mixture, which further reduces the solubility of the micelles containing the impurities. This leads to a further reduction in the cloud point temperature at which the micellar phase separates from the solution. Under these conditions, it is no longer necessary to heat the glycol-water mixture to achieve a flocculation of the impurities.

In an advantageous embodiment of the inventive method, the purified glycol-water mixture is passed, before being returned to the regeneration stage of the gas drying plant, through a basic second ion exchanger charged with hydroxide ions, the anions fed to the mixture in the first ion exchanger being at least partially replaced by hydroxide ions. Replacement of the acid anions by hydroxide ions prevents corrosion of the drying plant by the acid anions, in particular the chloride ions. A highly basic ion exchanger is preferably used. The replacement of acid anions by hydroxide anions is also described as desalination of the glycol. The second ion exchanger can be regenerated for example with sodium hydroxide solution.

In an advantageous embodiment of the present invention, the glycol-water mixture is passed through a sand or gravel filter to remove the flocculated impurities. A multi-stage filter is preferably used, the mixture first being passed through a coarser and then a finer sand fraction. The pressure rises as the filter becomes loaded with flocculated impurities. Then the sand filters have to be regenerated by back-flushing. Part of the purified glycol-water mixture can be used for this purpose.

A further embodiment of the present invention is an arrangement for drying a gas, in particular natural gas, using a glycol, which arrangement comprises an absorber in which the gas to be dried and glycol act upon each other. The absorber is linked to a means for removing the water-laden glycol from the absorber and for feeding the glycol to a reboiler for regenerating the glycol, a means for returning the regenerated glycol to the absorber, a mixing means coupled to the means for returning the regenerated glycol to said absorber, a means for removing part of the regenerated glycol, and a means for adding a predetermined amount of water, a settling chamber coupled to said mixing means, and a separating means coupled to said settling chamber for separating flocculated impurities, the separating means being coupled to the reboiler. The arrangement according to the invention is a side-stream method that conserves energy for drying the gas.

In one embodiment the device for returning the regenerated glycol to the absorber exhibits a storage vessel, the mixing device being connected to the storage vessel, preferably via a pump. A fine filter is used as the separating device.

An anion exchanger for pre-cleaning the glycol-water mixture is preferably integrated between the mixing device and the settling chamber.

According to a further feature of the present invention, an ion exchanger can be integrated between the mixing device and the separating device, anionic surfactants being removed from the glycol-water mixture in said ion exchanger.

A further embodiment of the invention is an arrangement for purifying glycol contaminated in a gas drying plant, wherein the gas drying plant contains a regeneration stage for driving out the water from a glycol-water mixture, the arrangement comprising a mixing means, a first ion exchanger, a filter means, and a regeneration stage means. The mixing means is used for mixing the glycol removed from the gas drying plant with water to form a glycol-water mixture, the first ion exchanger for removing anionic surfactants from the glycol-water mixture, and the filter means for removing flocculated impurities. The filter means may be located downstream of the first exchanger and coupled through a line to the regeneration stage for driving the -water out of the mixture.

In a preferred embodiment, the first ion exchanger is charged with anions of a strong acid, preferably with chloride ions.

An advantageous embodiment of the invention is characterised in that a basic, second ion exchanger filled with hydroxide ions is located downstream of the filter device to replace at least part of the anions fed to the glycol-water mixture in the first ion exchanger by hydroxide anions. This prevents an additional corrosive attack of the acid anions.

The filter device can exhibit a multi-stage sand or gravel filter in which coarser and downstream finer sand fractions are arranged one after the other. An active carbon filter can also be provided in addition. Both the first and the second anion exchanger and the filter device are equipped with devices (pipes, valves and corresponding control units) which permit back-flushing for regeneration or cleaning.

A preferred embodiment of the arrangement according to the present invention is characterised in that the mixing device is connected via a line to a pump of the gas drying plant passing the glycol to an absorber, that part of the glycol leaving the pump is pressed into the mixing device. Such a link-up of the purification cycle makes it possible to dispense with an additional pump in the purification cycle. Furthermore, the temperature of the glycol present in the gas drying plant cycle at this point is high enough to make it unnecessary to additionally warm the glycol to above the cloud point.

In the following the invention is described with the aid of an embodiment shown in the drawing.

DETAILED DESCRIPTION OF THE INVENTION

Figure 1:
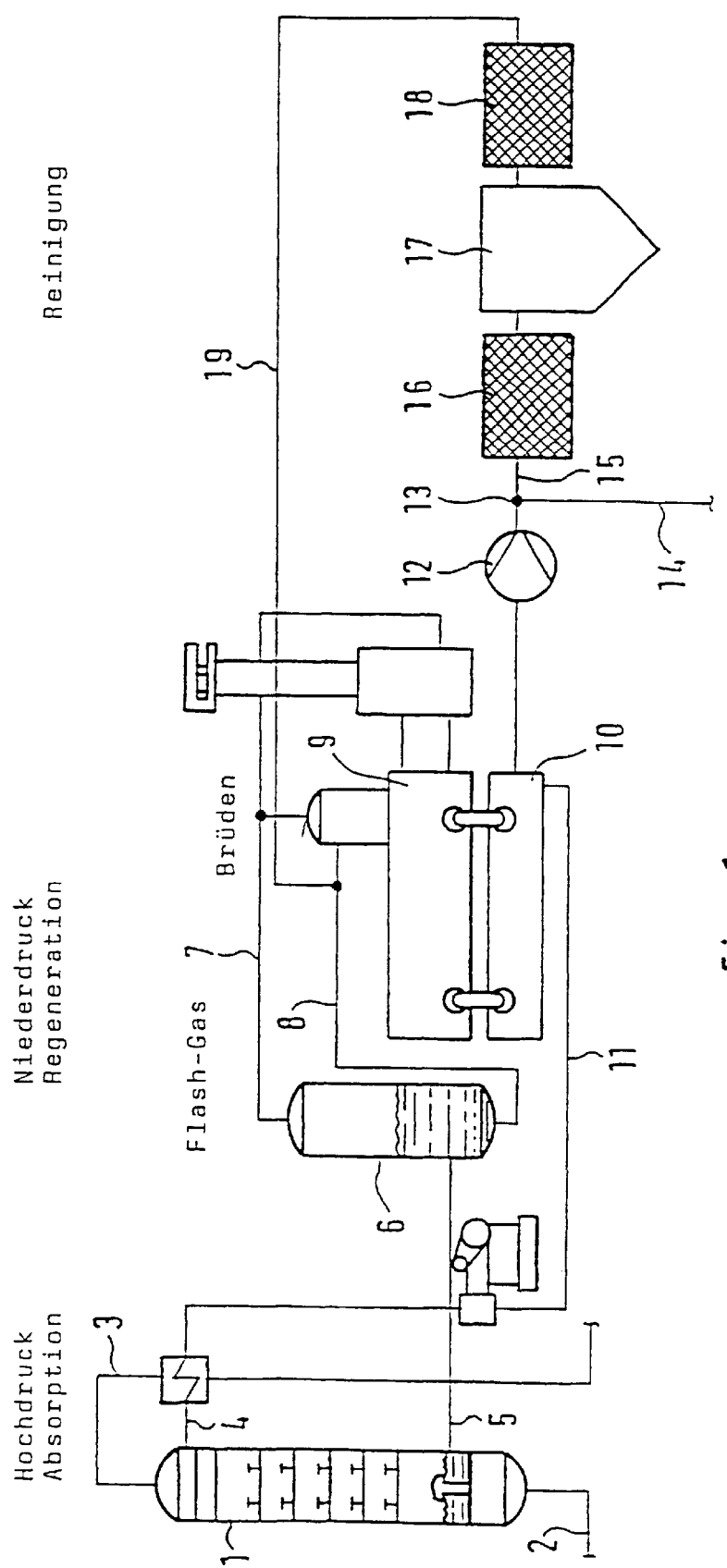
FIG. 1 shows a preferred embodiment of the inventive arrangement for drying a gas.

In FIG. 1 the gas to be dried is fed into one end of an absorber 1 via a line 2. The dried gas is removed from the other end of the absorber 1 via a line 3. The regenerated water-free glycol is fed via a line 4 to the end of the absorber 1 at which the dried gas is removed in order to achieve a countercurrent. The glycol passed in countercurrent in the absorber 1 absorbs the water from the gas as well as impurities. The contaminated glycol laden with water is removed via line 5 from the absorber and fed into a flash tank 6.

The laden glycol is retained in the flash tank where it gives off gas. The gas given off is removed via a line 7. The glycol laden with water is fed via line 8 to the working vessel of the reboiler 9. The glycol laden with water (the glycol-water mixture) is heated in the reboiler 9 and the water evaporates. The remaining regenerated glycol passes from the working vessel of the reboiler 9 to a storage vessel 10. The regenerated glycol is returned via lines 11 and 4 from the storage vessel 10 to the high-pressure absorber 1.

Parallel to this procedure of water absorption and glycol regeneration, the glycol is purified in a side-stream process.

To this end, part of the regenerated glycol is pumped out of the storage vessel via a pump 12 into a mixing device 13. The mixing device 13 is connected to a water supply line 14. The mixing device 13 mixes the glycol fed in via the pump 12 and the water fed in via the line 14 in an adjustable ratio.

The glycol-water mixture enters an anion exchanger 16 via a line 15 where it is precleaned. The anion exchanger contains for example a polymer resin of the type Dowex 1×8. The pre-cleaned glycol water mixture passes from the anion exchanger to the settling chamber 17 where it stays for a predetermined time at a predetermined temperature. During this time the impurities in the glycol flocculate. Pre-cleaning in the anion exchanger accelerates flocculation of the impurities, even with lower water contents. After flocculation of the impurities, the mixture is pumped out of the settling chamber 17 through a fine filter 18, the flocculated impurities being removed or separated.

The glycol-water mixture purified in this manner is returned to the reboiler via line 19. There the mixture is heated together with the water-laden glycol fed in via line 8, both the water absorbed from the gas and the water added from the mixing device 13 being evaporated;.

In a preferred embodiment of the inventive procedure, contaminated TEG is purified by mixing it with roughly the same amount of water. The mixture is then heated to a temperature of between 75 and 85° C. and kept at that temperature for about 15 minutes. A micellar phase predominantly containing impurities separates out. Then the mixture is filtered and the water is driven out in a reboiler at temperatures of between 185 and 205° C.

Figure 2:
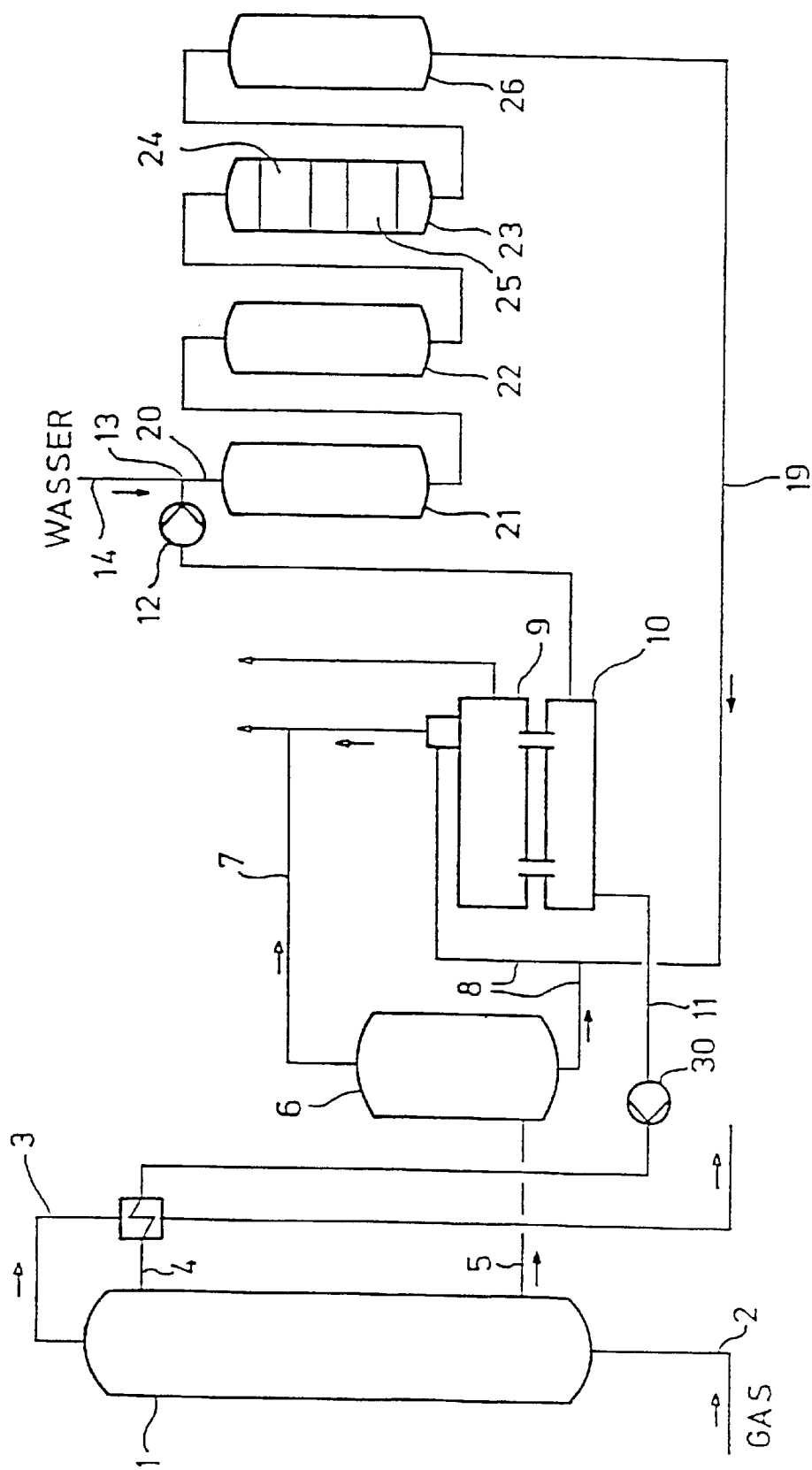
FIG. 2 shows a gas drying plant with an inventive arrangement for purifying the glycol contaminated in the gas drying plant.

In the gas drying plant in accordance with FIG. 2, the gas to be dried is fed via a line 2 into one end of an absorber 1. At the opposite end of the absorber 1 the dried gas is removed via the line 3. Regenerated, water-free glycol is fed in countercurrent via a line 4 to the end of the absorber 1 at which the dried gas is removed. The glycol passed in countercurrent in the absorber absorbs the water from the gas as well as impurities. The contaminated glycol laden with water is removed via a line 5 from the absorber and fed into a flash tank 6. The glycol laden with water is retained in the flash tank where it gives off gas. The gas given off is removed via a line 7. The glycol laden with water is fed via line 8 to the working vessel of the reboiler 9. The glycol laden with water (the glycol-water mixture) is heated in the reboiler 9, where the water evaporates. The remaining regenerated glycol passes from the working vessel of the reboiler 9 into a storage vessel 10. The regenerated dried glycol is fed from the storage vessel 10 via the line 11, the pump 30 and the line 4 to the absorber again.

Parallel to this method of water absorption and glycol regeneration, the glycol is purified in a side-stream process. In the embodiment depicted in FIG. 1, the purification cycle begins in the storage vessel 10. Part of the regenerated glycol is fed from the storage vessel via the pump 12 to a mixing device 13. The mixing device 13 is connected to a water supply line 14. The mixing device mixes the glycol fed in via the pump 12 and the water fed in via the line 14 in an adjustable ratio. The glycol fed in via pump 12 is preferably mixed with at least the same amount of water. It has been discovered that a higher proportion of water leads to faster clouding and flocculation of the impurities. On the other hand, a higher water content increases the amount of time and energy required to drive the water out of the mixture during regeneration. The necessary amount of water is therefore a question of optimisation; the glycol is preferably mixed with the water roughly in a ratio of 1:1.

The glycol-water mixture passes via line 20 to the first anion exchanger 21 which is filled with chloride anions. In the first anion exchanger a large part of the anionic surfactants (mainly carboxylic acid anions) of the glycol-water mixture is replaced by chloride ions. During this process the glycol-water mixture is at a temperature which is above the cloud point so the micellar phase separates. After the anionic surfactants have been removed, the micelles discharged in this way agglomerate. The cloud point is additionally reduced by the fact that the discharge of chloride ions into the mixture increases the mixture's ion strength and thus the solubility of the micelles is further reduced. Should the temperature of the glycol-water mixture in the anion exchanger 21 be below the cloud point, the mixture can be warmed as or after it leaves the ion exchanger 21.

The glycol-water mixture with flocculated impurities is then passed through a gravel or sand filter 22. The flocculated impurities are separated off there. In the embodiment depicted in FIG. 1, a second filter 23 is located downstream of the first sand filter 22, the second filter 23 being an active carbon filter 24 and a fine sand filter 25.

After the flocculated impurities have been removed, the glycol-water mixture is fed into a second anion exchanger 26. This strongly basic second anion exchanger 26 filled with hydroxide ions replaces the chloride ions brought into the glycol-water mixture through the first anion exchanger 21 by hydroxide ions. This is known as desalination. The chloride ions must be removed from the glycol as they may cause corrosion of the purification and gas drying plant. The second anion exchanger can be regenerated with a sodium hydroxide solution.

Following desalination, the glycol-water mixture is returned via line 19 to the regeneration stage of the gas drying plant where it is fed into the working vessel of the reboiler 9. There the water is driven out of the mixture. The regenerated, dried glycol is returned to the storage vessel 10.

Figure 3:
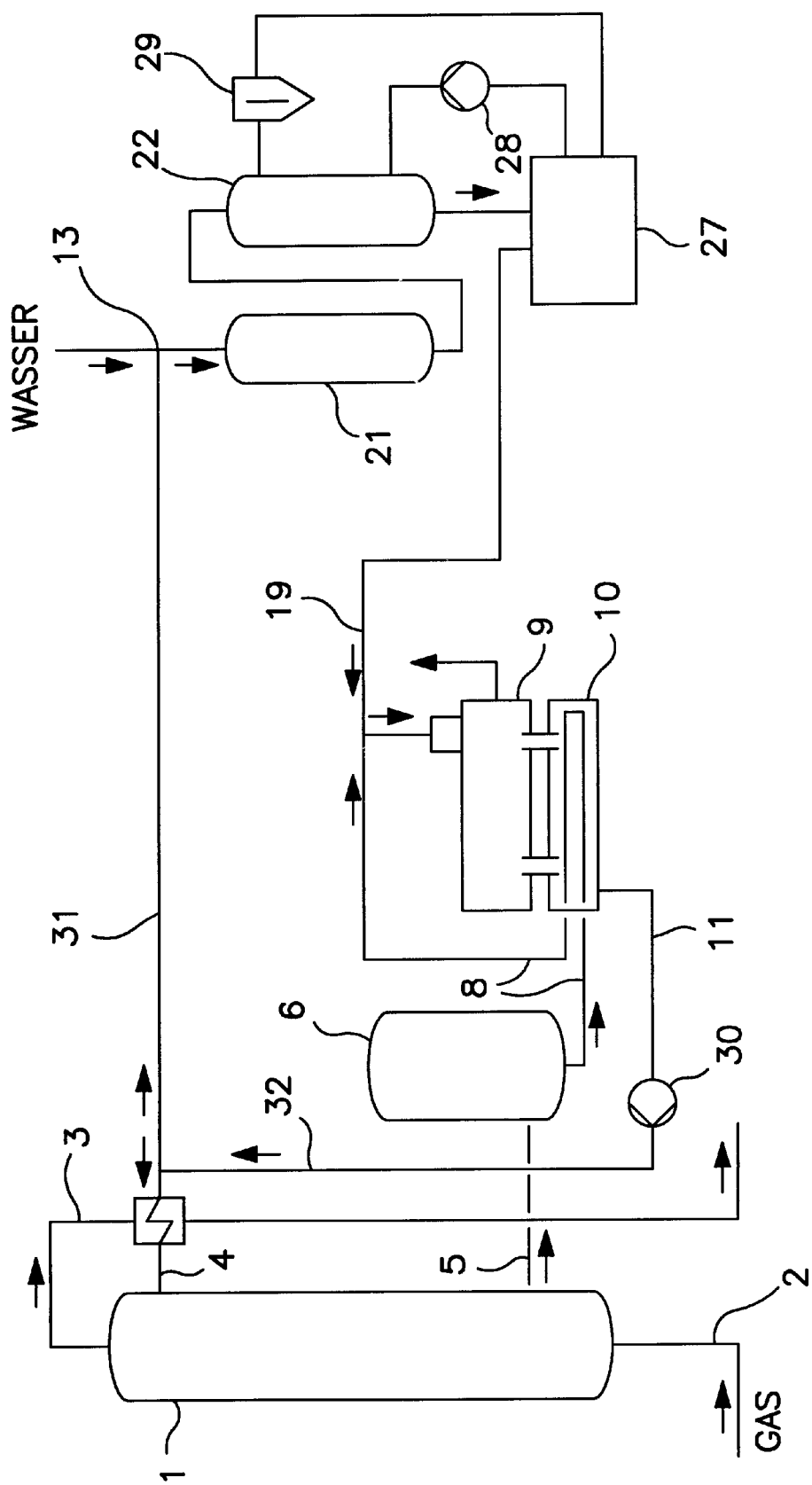
FIG. 3 shows a gas drying plant with an alternative embodiment of the inventive arrangement for purifying the glycol in a preferred link-up to the glycol cycle of the gas drying plant.

FIG. 3 shows a gas drying plant with a further embodiment of the inventive arrangement for purifying the glycol. Essentially, the gas drying plant corresponds to the one depicted in FIG. 2. The glycol is also purified here using the side-stream procedure. In contrast to the embodiment depicted in FIG. 2, however, in the plant according to FIG. 3 regenerated glycol is diverted downstream of pump 30 from line 32 through line 31. Downstream of the glycol pump 30, the glycol in line 32 is at a pressure which is high enough to pump the glycol through the glycol purification cycle. Therefore the additional pump 12 (FIG. 2) can be dispensed with.

The glycol is passed via line 31 to the mixing device 13 where water is added. Then the glycol-water mixture is passed through the anion exchanger 21. There the impurities take are flocculated and then filtered out in the sand filter 22. The glycol-water mixture passes from the sand filter 22 and enters a tank 27. From there it is returned for regeneration via line 19 to the working vessel of the reboiler 9.

The second anion exchanger for replacing the chloride ions by hydroxide ions is not shown in FIG. 2 to simplify the drawing. Furthermore, the sand filter is only depicted as a one-stage filter. Apart from the sand filter 22, FIG. 2 shows the devices for cleaning the sand filter 22 by back-flushing with a glycol-water mixture. The glycol-water mixture used for purification is pumped by pump 28 from the tank 27 in the reverse direction through the sand filter 22. The glycol-water mixture laden with impurities rinsed out of the sand filter is then passed through a filter device 29 and returned to the tank 27. The glycol-water mixture used for purification can be passed several times through this cycle.

A number of alternative embodiments are conceivable within the scope of the present invention. For example, the second anion exchanger used for desalination can be arranged between the first anion exchanger and the filter device or between two stages of the filter device. Furthermore, the purification procedure can also be integrated in the main-stream regeneration which is, however, only sensible for small amounts and severe contamination.

What is claimed is:

1. A method for drying a gas using a glycol, comprising
a) feeding the gas to an absorber,
b) bringing the gas into contact with the glycol in said absorber, the glycol absorbing at least part of the moisture and impurities from the gas,
c) removing the gas from said absorber,
d) removing the contaminated glycol laden with water and impurities from said absorber and regenerating the removed glycol by heating to drive the water out,
e) purifying at least part of the contaminated glycol removed from said absorber by
    mixing the contaminated glycol with at least half the amount of water,
    bringing the contaminated glycol-water mixture to a temperature above its cloud point,
    keeping the contaminated glycol-water mixture at said temperature for a predetermined time, during which time the impurities flocculate,
    removing the flocculated impurities,
    regenerating the glycol by driving the water out of the glycol-water mixture by heating, and
f) returning the regenerated glycol to said absorber.

2. The method according to claim 1 wherein, after the step of removing the flocculated impurities, the glycol-water mixture is mixed again and regenerated with the glycol which has been removed from the absorber and is to be regenerated.

3. The method according to claim 1 wherein the glycol-water mixture is filtered and/or centrifuged to remove the flocculated impurities.

4. The method according to claim 1 wherein the glycol-water mixture is passed over a first anion exchanger before heating, the anionic surfactants being removed from the mixture.

5. The method according to claim 1 wherein, during the purification of the glycol, the glycol-water mixture is brought to a temperature of approx. 40° C. to 90° C. and kept at that temperature for a period of between 2 and 30 minutes.

6. The method according to claim 5 wherein triethylene glycol is used and wherein, during the purification, the contaminated triethylene glycol is mixed with water in a ratio of roughly 1:1 and the triethylene glycol-water mixture is brought to a temperature of approximately 75° C. to 85° C. and kept at said temperature for a period of between 5 and 20 minutes.

7. A method for cleaning glycol contaminated in a gas drying plant, said method comprising the steps of:
removing contaminated glycol laden with water and impurities from the gas drying plant,
mixing the contaminated glycol with at least half the amount of water,
passing the contaminated glycol-water mixture over a first ion exchanger, during which anionic surfactants are removed from the glycol-water mixture,
reducing the cloud point below the temperature of the glycol-water mixture, thus leading to flocculation of the impurities,
removing the flocculated impurities,
returning the purified glycol-water mixture to a regeneration stage of the gas drying plant, and
driving the water out of the purified glycol-water mixture by heating.

8. The method according to claim 7 wherein the first ion exchanger is filled with anions of a strong acid, preferably chloride ions.

9. The method according to claim 7 wherein the purified glycol-water mixture is passed, before returning to a regeneration stage of the gas drying plant, through a basic second ion exchanger filled with hydroxide ions, the anions fed to the glycol-water mixture in the first ion exchanger being replaced at least partially by hydroxide ions.

10. The method according to claim 7 wherein the glycol-water mixture is passed through a sand or gravel filter to remove the flocculated impurities.

11. An apparatus for drying a gas, in particular natural gas, using a glycol, said apparatus comprising an absorber, in which a gas to be dried and the glycol can act upon each other, a means for removing glycol laden with water from said absorber and for feeding the glycol to a reboiler for regenerating the glycol, a means for returning the regenerated glycol to said absorber, a mixing means coupled to the means for returning the regenerated glycol to said absorber for removing part of the regenerated glycol and for adding a predetermined amount of water.

a settling chamber coupled to said mixing means, and a separating means coupled to said settling chamber for separating flocculated impurities, said separating means being coupled to said reboiler.

12. The arrangement according to claim 11 wherein an anion exchanger is coupled between said mixing means and said settling chamber for precleaning the glycolwater mixture.

13. The arrangement according to claim 11 wherein an anion exchanger is coupled between said mixing means and said separating means for removing anionic surfactants from the glycol-water mixture.

14. An arrangement of purifying glycol contaminated in a gas drying plant, wherein the gas drying plant contains a regeneration stage for driving out the water from a glycol-water mixture, said arrangement comprising:

a mixing means for mixing glycol removed from the gas drying plant with water to form a glycol-water mixture, a first ion exchanger coupled to said mixing means for removing anionic surfactants from the glycol-water, and a filter means for removing flocculated impurities from the glycol-water mixture arranged downstream of said first ion exchanger and coupled via a line to said regeneration stage.

15. The arrangement according to claim 14 wherein the first ion exchanger is filled with anions of a strong acid, preferably with chloride ions.

16. The arrangement according to claim 14 wherein a basic second ion exchanger filled with hydroxide ions for replacing at least part of the anions fed to the glycolwater mixture in said first anion exchanger by hydroxide ions is arranged downstream of said filter means.

17. The arrangement according to claim 14 wherein said mixing means is connected via a line in such a way with a pump of the gas drying plant feeding the glycol to an absorber that part of the glycol leaving said pump is pressed into said mixing means.

* * * * *